(12) United States Patent
Konno

(10) Patent No.: US 9,766,401 B2
(45) Date of Patent: Sep. 19, 2017

(54) DEFECT REVIEW APPARATUS AND METHOD FOR CORRECTING COORDINATE MISALIGNMENT USING TWO LIGHT SOURCES

(71) Applicant: Hitachi High-Technologies Corporation, Minato-ku, Tokyo (JP)

(72) Inventor: Takehiko Konno, Tokyo (JP)

(73) Assignee: Hitachi High-Technologies Corporation, Tokyo (JP)

(*) Notice: Subject to any disclaimer, the term of this patent is extended or adjusted under 35 U.S.C. 154(b) by 313 days.

(21) Appl. No.: 14/678,027

(22) Filed: Apr. 3, 2015

(65) Prior Publication Data
US 2015/0286001 A1 Oct. 8, 2015

(30) Foreign Application Priority Data
Apr. 8, 2014 (JP) .................. 2014-079544

(51) Int. Cl.
| | | |
|---|---|---|
| *H04N 7/18* | (2006.01) | |
| *G02B 6/255* | (2006.01) | |
| *G02B 21/36* | (2006.01) | |
| *G03F 7/20* | (2006.01) | |

(52) U.S. Cl.
CPC ......... *G02B 6/2555* (2013.01); *G02B 21/367* (2013.01); *G03F 7/7065* (2013.01)

(58) Field of Classification Search
CPC ........................... G02B 21/125; G02B 21/367
See application file for complete search history.

(56) References Cited

U.S. PATENT DOCUMENTS

2007/0024963 A1 2/2007 Maedo et al.
2013/0277553 A1 10/2013 Otani et al.

FOREIGN PATENT DOCUMENTS

| JP | 2007-19270 A | 1/2007 |
|---|---|---|
| JP | 2012-127848 A | 7/2012 |
| JP | 2013-148349 A | 8/2013 |

*Primary Examiner* — Young Lee
(74) *Attorney, Agent, or Firm* — Crowell & Moring LLP

(57) ABSTRACT

Provided is a defect review technique that can accurately correct coordinate differences with respect to unusual defects in which it is difficult to accurately correct coordinate misalignments by conventional automatic fine alignment. If it is impossible to correct a coordinate misalignment on the basis of a first optical microscope image acquired by a first light source, a defect review apparatus acquires a second optical microscope image using a second light source, and determines whether it is possible to correct the coordinate misalignment on the basis of the second optical microscope image.

11 Claims, 6 Drawing Sheets

DEFECT REVIEW APPARATUS AND METHOD FOR CORRECTING COORDINATE MISALIGNMENT USING TWO LIGHT SOURCES

CLAIM OF PRIORITY

The present application claims priority from Japanese patent application JP 2014-079544 filed on Apr. 8, 2014, the content of which is hereby incorporated by reference into this application.

BACKGROUND

Technical Field

The present invention relates to a defect review techniques for observing defects on samples detected by inspection devices to acquire detailed information of the observed defects.

Background Art

In manufacturing processes for such as semiconductor devices, processes such as film formation, lithographic exposure, or etching are repeated to form micro-circuit patterns on semiconductor samples via hundreds of processes (hereinafter, semiconductor samples are referred to as samples). In these manufacturing processes, decrease in yield rate may be caused by foreign particles generated on the sample due to errors or improper maintenances of process manufacturing devices or to mismatch in manufacturing conditions, or may be caused by abnormal appearances such as disconnection or short-circuiting of circuit patterns formed on the sample. Thus it is necessary to promptly identify the cause of foreign particles generated on the sample or of abnormal appearances of circuit patterns, and to take measures for them immediately. Hereinafter, foreign particles or abnormal appearances of circuit patterns will be referred to as defects.

As countermeasures for defects generated on samples in manufacturing processes of semiconductor devices, a method for estimating the cause of defects is known in which: the defect on the sample is detected by an inspection apparatus to acquire positional information of the defect; the defect on the sample is observed in details using electron microscopes (Scanning Electron Microscope, hereinafter referred to as SEM) according to the positional information; and if necessary, automatic classification of the defect is performed using ADC (Automatic Defect Classification) or elemental analysis is performed using EDS (Energy Dispersive X-ray Spectroscopy).

As inspection apparatuses, SEM-type inspection apparatuses and optical inspection apparatuses are known. SEM-type inspection apparatus: irradiates a primary electron beam onto the sample; acquires, by detecting a secondary electron generated from the sample, a SEM image of the defect portion; and acquires positional information of the defect according to a difference between the acquired SEM image and a SEM image of a reference portion. Optical inspection apparatus: irradiates light such as laser onto the sample; and detects reflected light or scattered light generated from the sample, thereby acquiring positional information of the sample.

Defect review apparatus, according to the positional information of the defect on the sample received from the inspection apparatus, rapidly acquires detailed information of the defect portion by a functionality referred to as ADR (Automatic Defect Review) that automatically captures SEM images of the defect portion.

Due to the difference of stage mechanical systems or of signal detection schemes between inspection apparatuses and defect review apparatuses, the defect coordinate systems generated in both apparatuses include misalignments from each other. Therefore, when the defect review apparatus attempts to acquire SEM images of the detect portion using the coordinate information of the defect received from the inspection apparatus only, the defect may be departed from the field of view of SEM. Thus a rough matching of coordinate system, referred to as global alignment, is typically performed between the inspection apparatus and the defect review apparatus before performing ADR. The global alignment is performed using alignment patterns or sample surface edges (edge portions). However, it is hardly likely that the defect is captured within the field of view of SEM only by global alignments.

In order to address the above-described problem, a method referred to as file alignment is used. Fine alignment is a method in which: coordinate information of representative defects on the sample is acquired before observing the sample using SEM; and the defect coordinate system defined by the inspection apparatus is converted into the defect coordinate system defined by the defect review apparatus. As a result of fine alignment, most of defects on the sample will be likely to be captured within the field of view of SEM. Fine alignment is particularly important as a method for correcting coordinates when observing defects on non-patterned samples, on which there is no specific patterns used for reference position alignment of defect coordinates and thus the defect coordinate acquired from the inspection apparatus is inaccurate.

Patent Document 1 listed below describes, regarding coordinate misalignments between inspection apparatus and defect review apparatus, that the defect is observed using a plurality of optical conditions (0013). It further describes as specific methods that an optical filter 514 and illumination intensities are adjusted (0077).

Patent Document 2 listed below describes a method for expanding the field of view to search defects in cases where the defect is not within the field of view even after performing fine alignment.

Patent Document 3 listed below describes about Dark Field Optical Microscope (DFOM). Fine alignment for non-patterned samples is typically performed using optical microscopes which field of view is wider than that of SEM. Specifically, DFOM is typically used which is capable of detecting micro defects by detecting scattered light. Patent Document 3 attempts, by adding light adjusting functionality such as dimming filter, deflecting filter, or wavelength filter, to correctly reflect the defect shapes onto DFOM images so that the reliability of coordinate correction is improved.

Regarding non-patterned samples which defect coordinates acquired from inspection apparatus is inaccurate, it is hardly likely that all defects for observation are captured within the field of view of SEM only by performing fine alignment to representative defects on the sample. Thus it is preferable to perform fine alignment to all defects for observation. Since there are tens to thousands of defects for fine alignment per sample, fine alignment is typically performed by automated sequences referred to as automatic fine alignment.

RELATED ART DOCUMENTS

Patent Documents

Patent Document 1: JP Patent Publication (Kokai) 2012-127848 A

Patent Document 2: JP Patent Publication (Kokai) 2007-019270 A

Patent Document 3: JP Patent Publication (Kokai) 2013-148349 A

SUMMARY

If defect review apparatus attempts to perform fine alignment with DFOM when observing non-patterned samples, there may be unusual defects that are barely captured in the field of view of DFOM, and there may be unusual defects which shapes cannot be reflected on the DFOM images even if the defect is captured within the field of view of DFOM. Examples of such unusual defects will be described below.

When observing a huge defect which size is over hundreds of μm, the coordinate information acquired by the inspection apparatus in detecting the huge defect may indicate a location that is departed by hundreds of μm from the coordinate system defined by the inspection apparatus, because the scattered light generated from the huge sample by illuminating laser light is too intensive. In such cases, when the defect review apparatus attempts to perform automatic fine alignment with DFOM according to the coordinate information acquired from the inspection apparatus, the huge defect is not captured within the field of view of DFOM and thus it is impossible to acquire SEM images of the huge defect with ADR. Even if the field of view is changed as described in Patent Document 2, there may arise reliability problems such as decrease in detection sensitivity after changing the field of view with the same optical conditions.

When illuminating laser light onto defects with low steps or onto defects with spot-like shapes, the scattered light includes anisotropy and may cause "tailing phenomenon" in which the tail of light is extended in one direction. Hereinafter, defects causing "tailing phenomenon" will be referred to as "tailing defect". Automatic fine alignment of DFOM performs coordinate corrections after performing image recognition of defects shapes reflected on the DFOM image. Thus if automatic fine alignment is performed for tailing defects, it is highly likely that the coordinate correction is positioned at the tail of light where no actual defect exists. In such cases, it is impossible to acquire SEM images of the tailing defect in ADR.

The present invention is made in the light of above-mentioned problems. It is an objective of the present invention to provide defect review techniques that can accurately correct coordinate differences with respect to unusual defects in which it is difficult to accurately correct coordinate misalignments by conventional automatic fine alignment.

If it is impossible to correct a coordinate misalignment on the basis of a first optical microscope image acquired by using a first light source, a defect review apparatus according to the present invention acquires a second optical microscope image using a second light source, and determines whether it is possible to correct the coordinate misalignment on the basis of the second optical microscope image.

With the defect review apparatus according to the present invention, it is possible to perform appropriate fine alignment to unusual defects in which it is difficult to perform appropriate fine alignment conventionally. Thus it is possible to improve throughput and reliability of SEM observation.

DETAILED DESCRIPTION OF THE EMBODIMENT(S)

Embodiment 1

Figure 1:
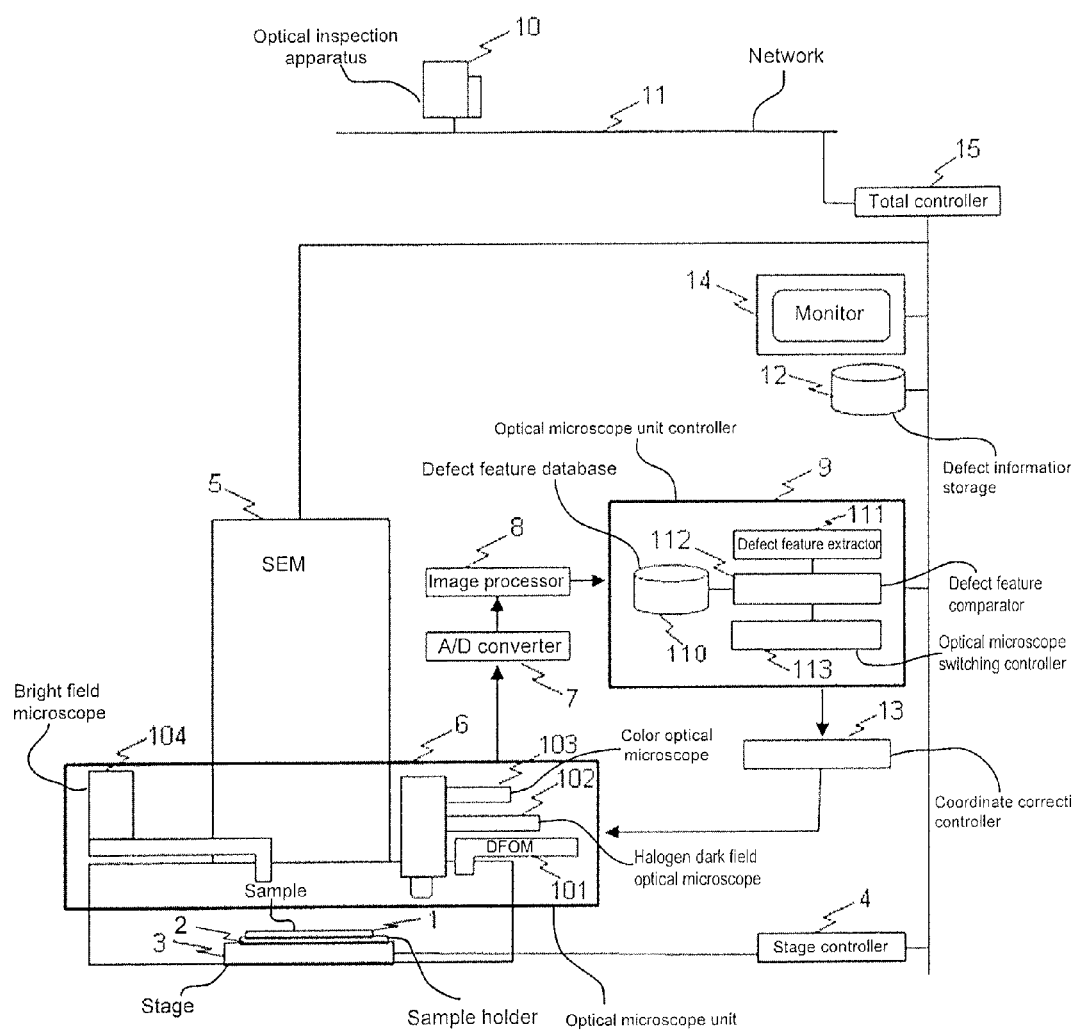
FIG. 1 is a diagram showing a configuration of defect review apparatuses according to embodiments 1 and 2.

FIG. 1 is a diagram showing a configuration of defect review apparatuses according to an embodiment 1 of the present invention. The defect review apparatus according to the embodiment 1 includes a sample holder 2, a stage 3, a stage controller 4, a SEM 5, an optical microscope unit 6, a A/D converter 7, an image processor 8, an optical microscope unit controller 9, a network 11, a defect information storage 12, a coordinate correction controller 13, a monitor 14, and a total controller 15.

The sample holder 2 holds a sample 1 to be inspected. The stage 3 moves the sample holder 2 so that the observed location is moved under the microscope. The stage controller 4 controls the stage 3. The SEM 5 observes defects on the sample 1 in details. The optical microscope unit 6 includes optical microscopes for optically detecting defects on the sample 1 to acquire accurate positional information. The A/D converter 7 converts, into digital signals, analog signals of such as reflected light or scattered light detected by the optical microscope unit 6. The image processor 8 creates images from the digital signals outputted from the A/D converter 7 and performs image processing such as binarization. The optical microscope unit controller 9 analyzes image data created by the image processor 8 to perform determination about defect coordinate corrections, and controls the optical microscope unit 6. The network 11 connects the defect review apparatus to upper systems such as an optical inspection apparatus 10. The defect information storage 12 stores defect information (such as coordinates, sizes, or category codes of defect) acquired from the inspection apparatus 10 via the network 11. The coordinate correction controller 13 corrects misalignments between the defect coordinate information stored in the defect information storage 12 and the defect coordinate information acquired by the defect review apparatus from coordinate corrections. The monitor 14 displays defect images and GUI (Graphical User Interface). The total controller 15 controls the total system such as the SEM 5 or the optical microscope unit 6.

The optical microscope unit 6 equips a plurality of types of optical microscopes. For example, the optical microscope unit 6 includes such as: a DFOM 101 that has been used for fine alignment conventionally; a dark field optical microscope of halogen light that is effective for decreasing background noises if the sample surface is highly reflective materials such as Cu or Poly; a color optical microscope 103 that is effective for checking differences of materials of films applied on the sample surface such as resist films or for checking amount of unevenness; and a bright field microscope 104 of halogen light that is used for positional alignment in reviewing patterned wafer. Each of the optical microscopes may include light sources and cameras respectively. Alternatively, if same types of light sources or cameras are used, those devices may be shared among the optical microscopes. The optical microscope unit 6 may select effective types of optical microscopes when performing fine alignment to observed defects. In addition, other types of optical microscopes may be used that are effective for fine alignment such as optical microscopes using LED (Light Emitting Diode) or metal halide lamps as light sources.

The optical microscope unit controller 9 includes a defect feature database (hereinafter, referred to as defect feature DB (Database)) 110, a defect feature extractor 111, a defect feature comparator 112, and an optical microscope switching controller 113.

The defect feature DB 110 stores defect features that are inappropriate to be used in fine alignment. The defect feature extractor 111 extracts defect features from the DFOM image of the defect outputted by the image processor 8. The defect feature comparator 112 compares the defect feature extracted by the defect feature extractor 111 with the defect feature stored in the defect feature DB 110, and calculates a degree of coincidence between these features. If the defect feature for observation matches with or is similar to the defect feature stored in the defect feature DB 110, the optical microscope switching controller 113 switches the current type of optical microscope into another type of optical microscope appropriate for fine alignment of observed defects. Details of the optical microscope unit controller 9 will be described later.

Figure 2:
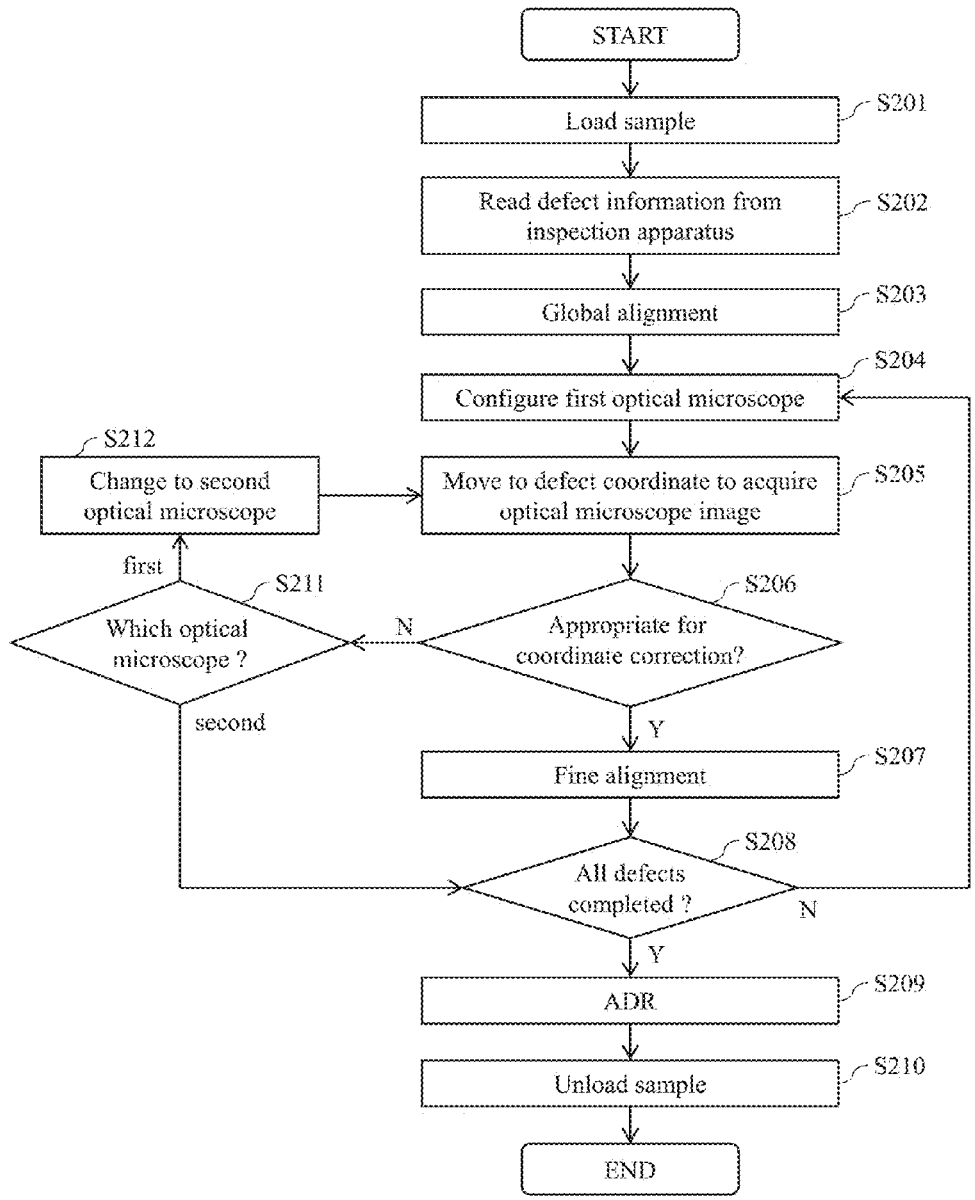
FIG. 2 is an overall process flowchart of the defect review apparatus.

FIG. 2 is an overall process flowchart of the defect review apparatus. Hereinafter, each step in FIG. 2 will be described.

(FIG. 2: Steps S201-S202)

The stage controller 4 loads the observed sample 1 onto the sample holder 2 in the defect review apparatus (S201). The optical microscope unit controller 9 acquires, via the network 11, information (coordinate, size, category code) of the defect on the sample 1, and stores the acquired information in the defect information storage 12. (S202)

(FIG. 2: Steps S203-S204)

By performing global alignment using the bright field optical microscope 104 of halogen light in the optical microscope unit controller 9, the coordinate correction controller 13 performs a first step of coordinate correction between the inspection apparatus 10 and the defect review apparatus (S203). The optical microscope unit controller 9 selects, as a first optical microscope used in fine alignment of a second step of coordinate correction, the DFOM 101 (S204). At this time, a laser light source is selected as the light source for the DFOM 101 and a camera for shooting dark field images is selected as the camera for the DFOM 101.

(FIG. 2: Step S205)

The stage controller 4 moves the field of view toward the coordinate of the observed defect according to the defect information (defect coordinate) acquired from the inspection apparatus 10 via the network 11 and stored in the defect information storage 12. The optical microscope unit controller 9 acquires an optical microscope image of the defect at the coordinate using the first optical microscope (the DFOM 101).

(FIG. 2: Steps S206-S207)

The optical microscope unit controller 9 determines whether the optical microscope image is appropriate for coordinate correction on the basis of the feature of the optical microscope image acquired by using the first optical microscope image (S206). If appropriate, the optical microscope unit controller 9 proceeds to step S207 to perform fine alignment. In not appropriate, the process proceeds to step S211. Details of step S206 will be described later with reference to FIG. 3.

(FIG. 2: Steps S208-S210)

The optical microscope unit controller 9 determines whether all observed defects have been reviewed (S208). If all defects have been reviewed, ADR is performed (S209) and the sample 1 is unloaded (S210). If not all defects have been reviewed, the process returns to step S204. Then the optical microscope unit controller 9 switches the type of optical microscope into the first optical microscope, and the same processes will be performed for the next defect coordinate acquired from the inspection apparatus 10.

(FIG. 2: Steps S211-S212)

If the first optical microscope is currently used, the optical microscope unit controller 9 proceeds to step S212 to switch the optical microscope into the second optical microscope. Then the process returns to step S205, and the same processes will be performed for the same defect coordinate again using the second optical coordinate. If the second optical coordinate is currently used, the process proceeds to step S208.

Figure 3:
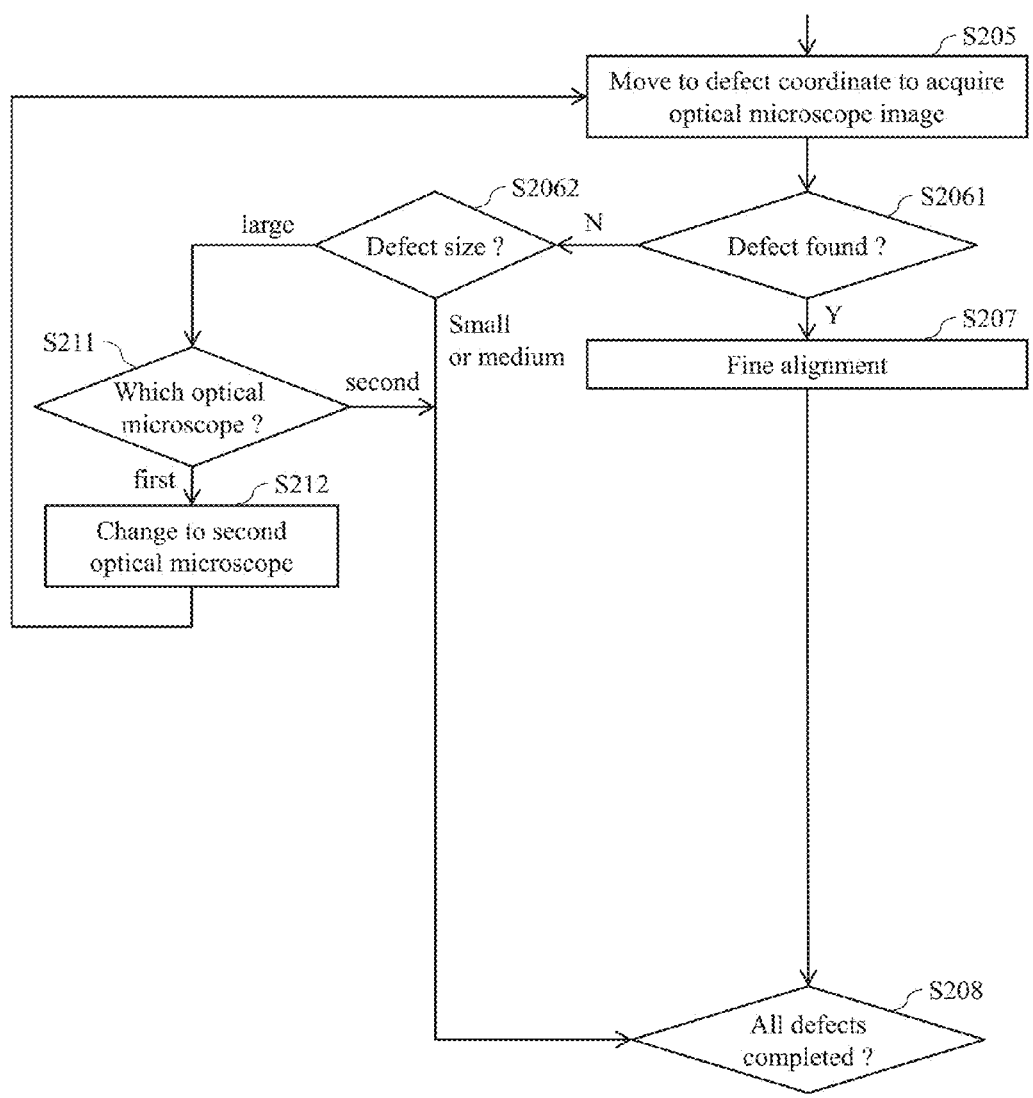
FIG. 3 is a flowchart showing details of step S206 with respect to a huge defect 402.

FIG. 3 is a flowchart showing details of step S206 with respect to a huge defect 402. For the sake of simplicity of description, parts of steps described in FIG. 2 are omitted, and steps around step S206 only are described. Hereinafter, each step in FIG. 3 will be described.

(FIG. 3: Step S2061)

The optical microscope unit controller 9 determines, according to the feature of the optical microscope image acquired by using the first optical microscope, whether the optical microscope image includes defects. If defect is found, the process proceeds to step S207. Otherwise the process proceeds to step S2062.

(FIG. 3: Step S2062)

The optical microscope unit controller 9 refers to the defect information stored in the defect information storage 12, and acquires the defect size acquired by the inspection apparatus 10 at the current coordinate of the field of view. If the defect is a huge defect which size is such as over hundreds of μm, the process proceeds to step S211. If the defect size is small to medium such as below hundreds of μm, the process proceeds to step S208. Alternatively, the optical microscope unit controller 9 may acquire the category code assigned by the inspection apparatus 10 at the current coordinate of field of view. If the category code corresponds to a huge defect such as over hundreds of μm, the process proceeds to step S211. If the defect size is small to medium such as below hundreds of μm, the process proceeds to step S208.

(FIG. 3: Steps S2062: Additional Note)

As described above, if the defect is a huge defect which size is over hundreds of μm, the inspection apparatus 10 may detect a location as the defect coordinate which is departed by hundreds of μm from the defect. In other words, the defect that is assumed to be found may not be found in step S2061 depending on the defect size. Thus in this step, it is determined whether the DFOM 101 is appropriate for coordinate correction according to the defect information (defect size, category code) stored in the defect information storage 12.

(FIG. 3: Step S212)

The optical microscope unit controller 9 switches the optical microscope from the DFOM 101 to the halogen bright field optical microscope 104. The halogen bright field optical microscope 104 is an optical microscope that is used for searching alignment marks when performing alignment for patterned samples. The halogen bright field optical microscope 104 has a field of view 4 to 9 times larger than that of the DFOM 101. Thus it is possible to capture, within the field of view, huge defects that exist at a location departed by hundreds of μm from the location observed by the DFOM 101. Although the signal detected by the halogen bright field optical microscope 104 is not scattered light but reflected light, it is possible to sufficiently identify the defect because of the huge defect size.

Figure 4:
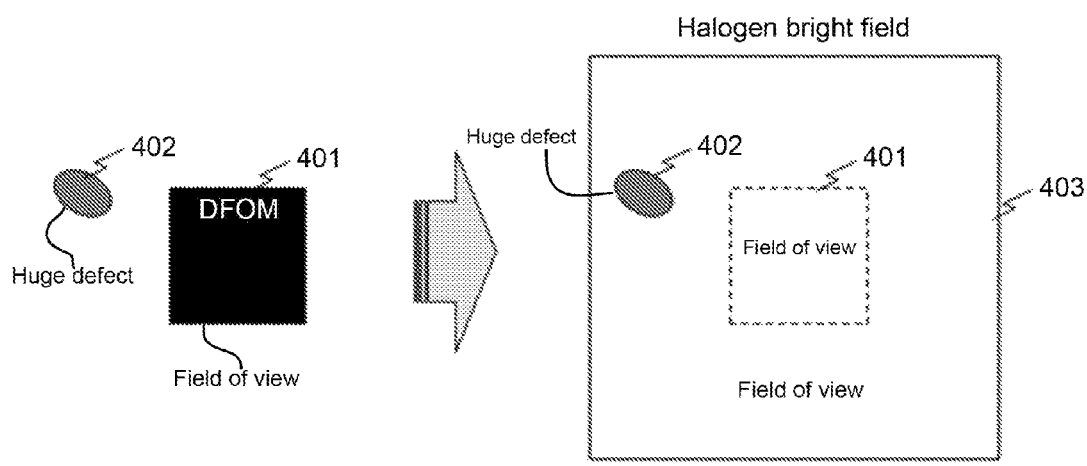
FIG. 4 is an image diagram showing an example where fine alignment is performed to the huge defect 402.

FIG. 4 is an image diagram showing an example where fine alignment is performed to the huge defect 402. When acquiring the optical microscope image by the DFOM 101 in step S206 of FIG. 3, the huge defect 402 exists at a location departed by hundreds of μm from the field of view 401 of the DFOM 101. Thus it is impossible to appropriately perform fine alignment. By switching the optical microscope into the halogen bright field optical microscope 104, the field of view 403 becomes 4 to 9 times larger than the field of view 401 of the DFOM 101. This enables observing the huge defect 402 located within the field of view even if the coordinate of the huge defect 402 acquired by the inspection apparatus 402 is misaligned from the actual defect coordinate.

Embodiment 1: Summary

As discussed thus far, if it is impossible to observe the defect using the DFOM 101, the defect review apparatus according to the embodiment 1 checks the defect size on the basis of the defect information, and switches the DFOM 101 into the halogen bright field optical microscope 104 if the defect is a huge defect. Accordingly, even in cases where the inspection apparatus 10 observes huge defects which coordinate is difficult to be precisely acquired, the halogen bright field optical microscope 104 acquires precise coordinates and the coordinate correction controller 13 may correct the coordinate misalignment according to the precisely acquired coordinates.

It can be assumed that only the DFOM 101 may be used as another method for performing fine alignment with respect to huge defects and a search-around functionality may be used. In other words, the field of view is rotationally changed until the defect is found to search the defect, thereby acquiring the correct coordinate of the huge defect. However, the search-around functionality has a problem in that the throughput time is large. In addition, erroneous detection may more frequently occur during the search-around if the sample may cause large background noises. Therefore, the method according to the embodiment 1 may be effective for huge defects.

Embodiment 2

In the embodiment 1, an example of huge defect is described as a defect which coordinate-misalignment between the inspection apparatus 10 and the defect review apparatus is difficult to be corrected. In an embodiment 2 of the present invention, as a defect which coordinate-misalignment is difficult to be corrected, an example of tailing defect will be described. The configuration of the defect review apparatus is the same as that of the embodiment 1. Thus the operation for tailing defects will be mainly described.

Figure 5:
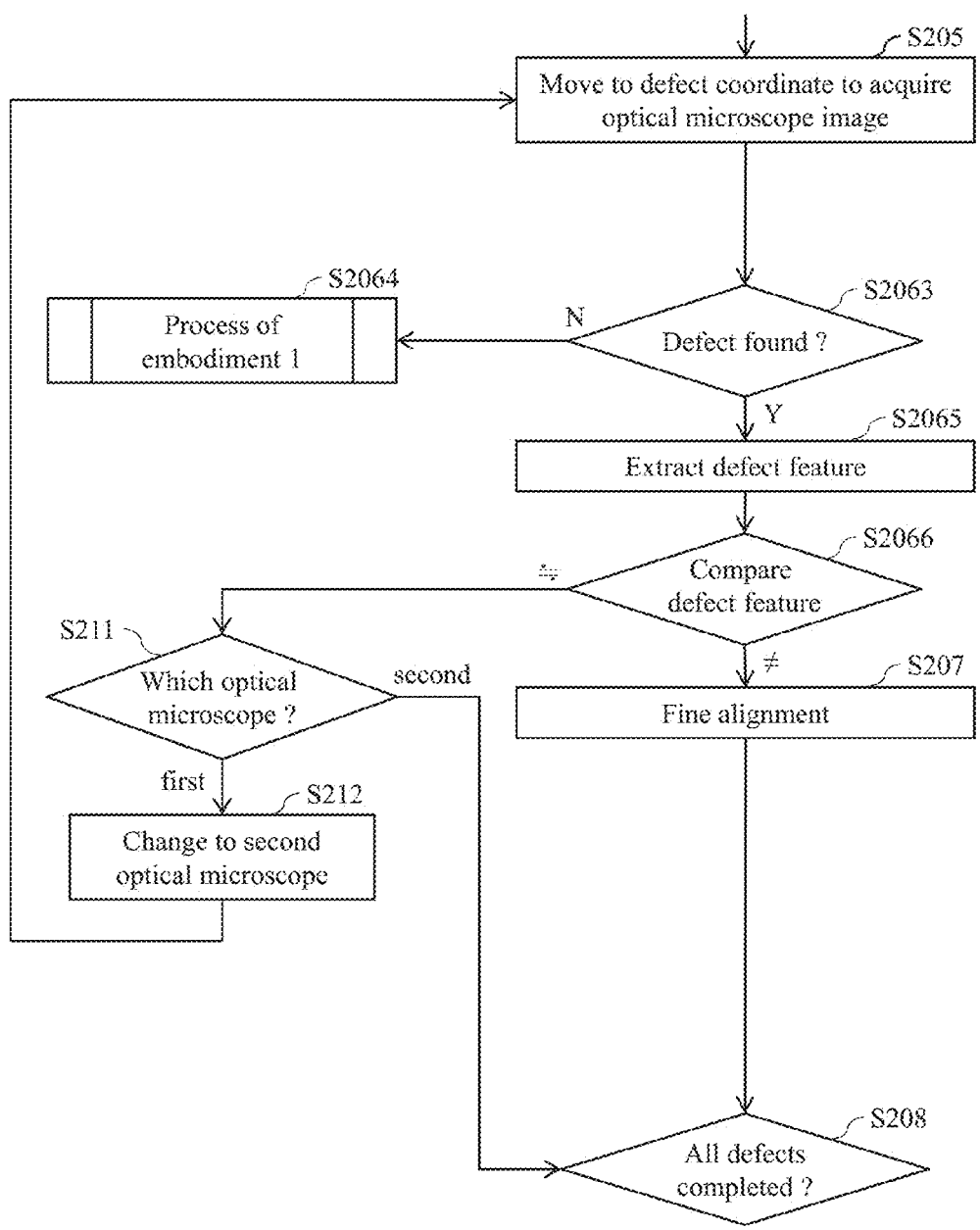
FIG. 5 is a flowchart showing details of step S206 with respect to a tailing defect 601.

FIG. 5 is a flowchart showing details of step S206 in the embodiment 2. As in FIG. 3, parts of steps described in FIG. 2 are omitted and steps around step S206 only are described. Hereinafter, each step in FIG. 5 will be described.

(FIG. 5: Steps S2063-S2064)

The optical microscope unit controller 9 determines whether the optical microscope image acquired by using the first optical microscope includes defects (S2063). If defect is found, the process proceeds to step S2065. Otherwise the process proceeds to step S2064. In step S2064, the optical microscope unit controller 9 may perform the same processes as those after step S2062 described in the embodiment 1. Alternatively, the optical microscope unit controller 9 may perform some error handlings and return to step S205, then may perform the same processes for the next defect coordinate.

(FIG. 5: Step S2065)

The defect feature extractor 111 extracts defect features from the optical microscope image acquired by using DFOM 101. The defect features are several to tens of types of features such as defect size, brightness, circularity, or anisotropy, graded and numerized into such as 10 levels. For example, features of circular and huge foreign particle may be numerized such as: size and brightness are both level 10; circularity is level 10; and anisotropy is level 1.

(FIG. 5: Step S2066)

The defect feature comparator 112 compares the observed defect feature extracted in step S2065 with the defect features that are not appropriate for fine alignment stored in the defect feature DB 110. If the difference between those features is within a predetermined threshold (i.e. those defects are similar to each other), the process proceeds to step S211. Otherwise the process proceeds to step S207.

(FIG. 5: Steps S2066: Additional Note)

As described above, in case of tailing defects, the inspection apparatus 10 may erroneously align the coordinate at the tail portion. Thus in this step, the defect feature of tailing defects is stored in the defect feature DB 110 in advance. If the defect feature matches with the stored feature, it is determined that the defect is not appropriate for coordinate misalignment correction using the DFOM 101. Regarding defects other than tailing defects that are not appropriate for coordinate misalignment correction by using the DFOM 101, the defect feature of such defects may also be stored in the defect feature DB 110 in advance and such defects may be excluded from fine alignment process in this step.

(FIG. 5: Step S212)

The optical microscope unit controller 9 switches the optical microscope from the DFOM 101 into the halogen dark field optical microscope 102 or into the color optical microscope 103. When using the halogen dark field optical microscope 102 or the color optical microscope 103, it is commonly known that no tailing phenomenon that is observed in using the DFOM 101 will occur and that the coordinate misalignment may be precisely corrected with respect to the actual defect. Thus in the embodiment 2, the DFOM 101 is switched into the halogen dark field optical microscope 102 or into the color optical microscope 103. The optical microscope unit controller 9 selects a halogen light source and a camera for shooting dark fields when using the halogen dark field optical microscope 102, and selects halogen light source and a camera for shooting color images when using the color optical microscope 103.

Figure 6:
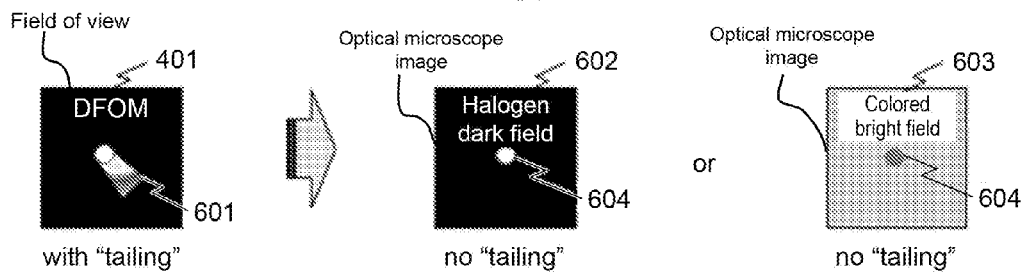
FIG. 6 is an image diagram showing an example where fine alignment is performed to the tailing defect 601.

FIG. 6 is an image diagram showing an example where fine alignment is performed to the tailing defect 601. When acquiring the optical microscope image by using the DFOM 101 in step S205 of FIG. 2, a tailing phenomenon 601 occurs in the field of view 401 of the DFOM 101. Thus it is highly likely that the coordinate correction is positioned at the light tail in fine alignment process. By switching the optical microscope into the halogen dark field optical microscope 102 or into the color optical microscope 103, the tailing phenomenon occurring in the field of view 401 of the DFOM 101 will not occur as shown in the optical microscope images 602 and 603. Thus it is possible to appropriately correct coordinate at the actual position of defect 604.

Figure 7:
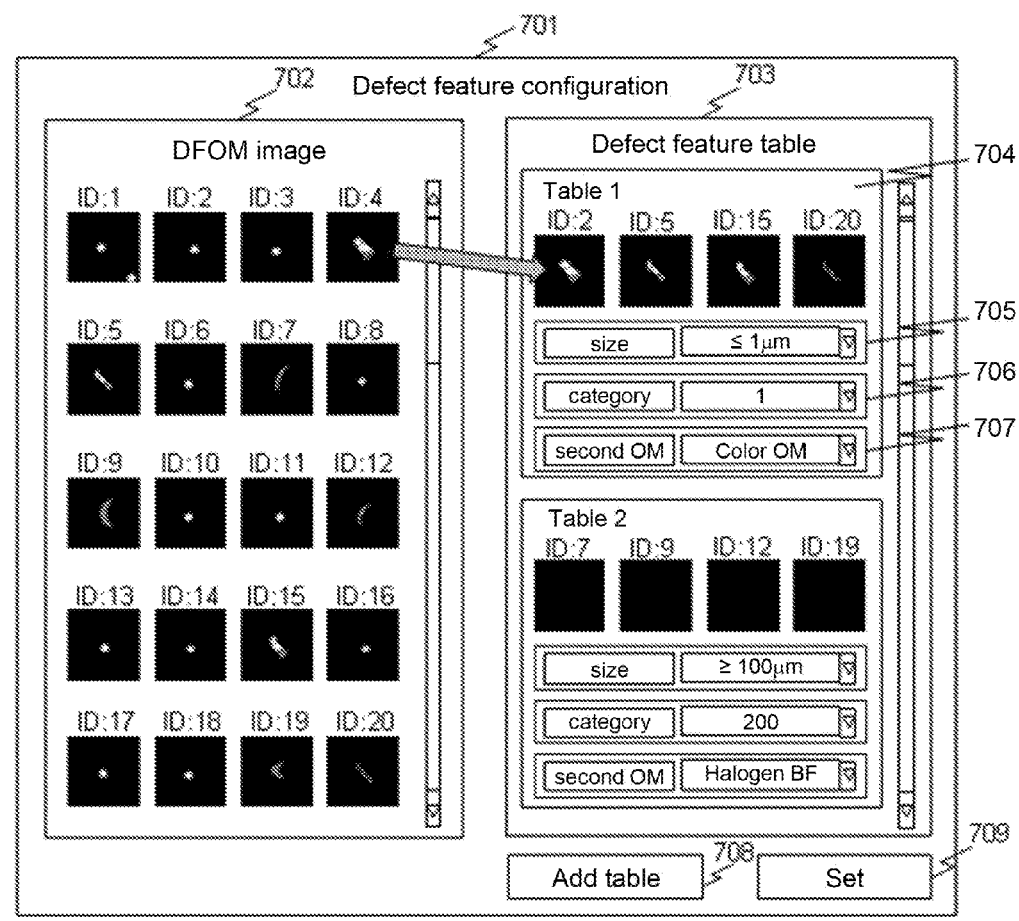
FIG. 7 is a display image of a defect feature configuration screen 701 provided by an optical microscope unit controller 9 on a monitor 14.

FIG. 7 is a display image of a defect feature configuration screen 701 provided by the optical microscope unit controller 9 on the monitor 14. A user may use the defect feature configuration screen 701 to register defect features that are not appropriate for fine alignment into the defect feature DB 110 in advance.

The defect feature configuration screen 701 displays, at the left side of the display, an image list 702 of defects acquired in fine alignment. The defect feature configuration screen 701 displays, at the right side of the display, a table list 703 for registering defect images that are not appropriate for fine alignment for each of defect types. The operator selects a defect image that is not appropriate for fine alignment from the defect image list 702. The operator copies, by drag & drop operation, the selected defect image into the table 704 for each of defect types created at the right side of the screen. After copying the images into each of the tables 704, size thresholds 705 or category codes 706 corresponding to the defect registered in the table 704 may be configured if necessary. By configuring the size threshold 705 or the category code 706, it is possible to determine whether the defect is appropriate for fine alignment according to the size or the category information of the observed defect acquired from the inspection apparatus 10. When creating a new table, the operator pushes a table add button 708.

For example, when determining a defect having a feature registered in the table 1 shown in FIG. 7, it is determined that the defect is not appropriate for fine alignment, if: the defect has a defect feature commonly seen in collected defect images; the defect size is at or below 1 μm; and the category information is 1. If the observed defect matches with or is similar to the defect feature registered in each of the tables 704, the type 707 of optical microscope used as the second optical microscope is configured in each of the tables 704. When the operator pushes the configuration button 709, the defect feature extractor 111 extracts features commonly seen in defects registered in each of the tables 704, and registers the extracted feature in the defect feature DB 110 along with each of the input items.

Embodiment 2: Summary

As discussed thus far, if it is impossible to observe the defect using the DFOM 101, the defect review apparatus according to the embodiment 2 compares the defect feature with the features stored in the defect feature DB 110 in advance. If those features match with each other, the DFOM 101 is switched into the halogen dark field optical microscope 102 or into the color optical microscope 103. Accordingly, even in cases where the inspection apparatus 10 observes tailing defects which coordinate may be positioned at wrong coordinate, the halogen dark field optical microscope 102 or the color optical microscope 103 may position the correct coordinate and the coordinate correction controller 13 may correct the coordinate misalignment according to the precisely positioned coordinates.

It can be assumed that the type of optical microscope may not be changed and only the image processing may be used to avoid positional misalignment as another method for performing fine alignment with respect to tailing defects. For example, with respect to defects causing phenomenon in which light extends in one direction that is characteristic in tailing defects, the coordinate positioning may be corrected in the direction opposite to the direction to which the tail is extended. However, it is difficult in this method to determine the portion from which the tail extends and the portion at which the tail end. Thus there is a problem in that the reliability in determining the actual defect is low. Thus it is preferable to correct the coordinate misalignment after changing the type of optical microscope so that the proper defect shape is reflected into the optical microscope image, as in the embodiment 2.

The present invention is not limited to the embodiments, and various modified examples are included. The embodiments are described in detail to describe the present invention in an easily understood manner, and the embodiments are not necessarily limited to the embodiments that include all configurations described above. Part of the configuration of an embodiment can be replaced by the configuration of another embodiment. The configuration of an embodiment can be added to the configuration of another embodiment. Addition, deletion, and replacement of other configurations are also possible for part of the configurations of the embodiments.

The configurations, the functions, the processing units, the processing means, etc., may be realized by hardware such as by designing part or all of the components by an integrated circuit. A processor may interpret and execute programs for realizing the functions to realize the configurations, the functions, etc., by software. Information, such as programs, tables, and files, for realizing the functions can be stored in a recording device, such as a memory, a hard disk, and an SSD (Solid State Drive), or in a recording medium, such as an IC card, an SD card, and a DVD.

DESCRIPTION OF SYMBOLS

1 sample
2 sample holder
3 stage
4 stage controller
5 SEM
6 optical microscope unit
7 A/D converter
8 image processor
9 optical microscope unit controller
10 inspection apparatus
11 network
12 defect information storage
13 coordinate correction controller
14 monitor
15 total controller
101 DFOM
102 halogen dark field optical microscope
103 color optical microscope
104 halogen bright field optical microscope
110 defect feature DB
111 defect feature extractor
112 defect feature comparator
113 optical microscope switching controller
701 defect feature configuration screen
702 defect image list
703 table list
704 table
705 size threshold input area
706 category code input area 707 optical microscope type input area
708 table add button
709 configuration button

What is claimed is:

1. A defect review apparatus that acquires a defect image on a sample according to coordinate information of a defect on the sample detected by an inspection apparatus, comprising:
   an optical microscope unit that creates an optical microscope image of the defect using a signal generated by irradiating light onto the sample;
   a defect information storage that stores defect information describing a coordinate of the defect that is acquired by the inspection apparatus when detecting the defect on the sample; and
   an optical microscope controller that corrects a coordinate misalignment between the inspection apparatus and the defect review apparatus according to an optical microscope image acquired by using the optical microscope unit;
   wherein the optical microscope unit includes a first and a second light sources each irradiating different types of light from each other,
   wherein the optical microscope controller determines, according to a feature of a first optical microscope image acquired by the optical microscope unit using the first light source with respect to a coordinate of the defect described in the defect information, whether it is possible to correct a coordinate misalignment between the inspection apparatus and the defect review apparatus using the first optical microscope image,
   wherein if the first optical microscope image is not appropriate for coordinate correction, the optical microscope controller switches the first light source into the second light source to acquire a second optical microscope image,
   and wherein the optical microscope controller determines whether it is possible to correct the coordinate misalignment using the second optical microscope image.

2. The defect review apparatus according to claim 1,
   wherein the optical microscope unit includes a laser light source used for creating a dark field image as the first light source and includes a halogen light source for creating a halogen bright field image as the second light source,
   wherein the defect information describes a size of the defect detected by the inspection apparatus,
   and wherein if the optical microscope controller determines that the defect is not included in the first optical microscope image according to a feature of the first optical microscope image, the optical microscope controller acquires a size of the defect described in the defect information, switches the first light source into the second light source to acquire the second optical microscope image if the acquired size is at or above a predetermined value, and determines whether it is possible to correct the coordinate misalignment using the second optical microscope image.

3. The defect review apparatus according to claim 2,
   wherein the defect information describes a category code indicating a size of the defect or a type of the defect,
   and wherein if the optical microscope controller determines that the defect is not included in the first optical microscope image according to a feature of the first optical microscope image, the optical microscope controller acquires a category code of the defect described in the defect information, switches the first light source into the second light source to acquire the second optical microscope image if the acquired category code corresponds to a predetermined defect type, and determines whether it is possible to correct the coordinate misalignment using the second optical microscope image.

4. The defect review apparatus according to claim 1,
   wherein the defect review apparatus comprises a feature storage that stores feature information describing a feature of an optical microscope image which is not appropriate for using in correcting the coordinate misalignment,
   wherein the optical microscope unit includes a laser light source and a light-receiving camera used for creating a dark field image as the first light source and includes a halogen light source and a light-receiving camera used for creating a halogen dark field image or for creating a color image as the second light source,
   and wherein the optical microscope controller switches the first light source into the second light source to acquire the second optical microscope image if a difference between a feature of the first optical microscope image and a feature described in the feature information is within a predetermined range, and determines whether it is possible to correct the coordinate misalignment using the second optical microscope image.

5. The defect review apparatus according to claim 4,
   wherein the feature information describes, as the feature of an optical microscope image which is not appropriate for using in correcting the coordinate misalignment, a feature of a tailing optical microscope image which scattered light has anisotropy,
   and wherein the optical microscope controller switches the first light source into the second light source to acquire the second optical microscope image if a difference between a feature of the first optical microscope image and a feature of the tailing optical microscope image is within a predetermined range, and determines whether it is possible to correct the coordinate misalignment using the second optical microscope image.

6. The defect review apparatus according to claim 4,
   wherein the optical microscope unit includes, as the second light source, a halogen light source for creating a color image, and further includes a first camera that shoots the dark field image and a second camera that shoots the color image,
   and wherein the optical microscope unit switches the first camera into the second camera when switching the first light source into the second light source.

7. The defect review apparatus according to claim 4,
   wherein the defect review apparatus includes a feature extractor that extracts a feature from the dark field image,
   and wherein the optical microscope controller categorizes a feature extracted by the feature extractor, assigns a category ID to the extracted feature, and stores the extracted feature in the feature storage as the feature information.

8. The defect review apparatus according to claim 7,
   the defect review apparatus includes an operation interface that provides a GUI for updating the feature information,
   wherein the operation interface includes an item to select a feature of the first optical microscope image that is not appropriate for correcting the coordinate misalignment from the feature information, and wherein the operation interface includes an item to specify the second light source to be switched from the first light source.

9. The defect review apparatus according to claim 8, wherein the operation interface further includes an item to configure a size threshold and a category code of a defect that is not appropriate for using in correcting the coordinate misalignment.

10. The defect review apparatus according to claim 1, wherein the optical microscope unit includes a plurality of the second light source, wherein the optical microscope controller includes a correspondence table describing a relationship between a feature of the first optical microscope image and the second light source to be used in correcting the coordinate misalignment, and wherein the optical microscope controller identifies the second light source that is to be used in correcting the coordinate misalignment according to the correspondence table.

11. A method for reviewing a defect using a defect review apparatus that acquires a defect image on a sample according to coordinate information of the defect on the sample detected by an inspection apparatus, the defect review apparatus comprising an optical microscope unit that creates an optical microscope image of the defect using a signal generated by irradiating light onto the sample, the optical microscope unit comprising a first and a second light sources each irradiating different types of light from each other, the method comprising:

a step of reading defect information from a defect information storage that stores the defect information describing a coordinate of the defect that is acquired by the inspection apparatus when detecting the defect on the sample; and an optical microscope controlling step of correcting an coordinate misalignment between the inspection apparatus and the defect review apparatus according to an optical microscope image acquired by using the optical microscope unit;

wherein the optical microscope controlling step further includes a step of determining, according to a feature of a first optical microscope image acquired by the optical microscope unit using the first light source with respect to a coordinate of the defect described in the defect information, whether it is possible to correct a coordinate misalignment between the inspection apparatus and the defect review apparatus using the first optical microscope image, wherein if it is determined in the optical microscope controlling step that the first optical microscope image is not appropriate for coordinate correction, the optical microscope controlling step further includes a step of switching the first light source into the second light source to acquire a second optical microscope image, and wherein the optical microscope controlling step further includes a step of determining whether it is possible to correct the coordinate misalignment using the second optical microscope image.

* * * * *